US008334277B2

(12) United States Patent
Kang et al.

(10) Patent No.: US 8,334,277 B2
(45) Date of Patent: Dec. 18, 2012

(54) {4-[2-(DIMETHYLAMINO)-1-(1-HYDROXYCYCLOHEXYL)ETHYL]PHENOXY}PHOSPHATE OR A PHARMACEUTICALLY ACCEPTABLE SALT THEREOF, A PRODUCTION METHOD THEREFOR AND A PHARMACEUTICAL COMPOSITION FOR PREVENTING AND TREATING CENTRAL NERVOUS SYSTEM DISORDERS CONTAINING THE SAME AS AN ACTIVE COMPONENT

(75) Inventors: Seok Won Kang, Hwaseong-si (KR); Jong Soo Chun, Yongin-si (KR); Heung Mo Kang, Seoul (KR); Eui Seok Hong, Ansan-si (KR); Kwang-Woo Chun, Yongin-si (KR); Young Seok Byun, Yongin-si (KR); Myung-Hwa Kim, Yongin-si (KR); Young Il Moon, Anyang-si (KR); Jei Man Ryu, Anyang-si (KR)

(73) Assignee: JE IL Pharmaceutical Co., Ltd., Seoul (KR)

( * ) Notice: Subject to any disclaimer, the term of this patent is extended or adjusted under 35 U.S.C. 154(b) by 120 days.

(21) Appl. No.: 12/990,972

(22) PCT Filed: May 8, 2009

(86) PCT No.: PCT/KR2009/002426
§ 371 (c)(1),
(2), (4) Date: Nov. 4, 2010

(87) PCT Pub. No.: WO2009/136756
PCT Pub. Date: Nov. 12, 2009

(65) Prior Publication Data
US 2011/0059923 A1  Mar. 10, 2011

(30) Foreign Application Priority Data
May 8, 2008 (KR) .................. 10-2008-0043034

(51) Int. Cl.
*A61K 31/045* (2006.01)
*A61K 31/137* (2006.01)
*A61K 31/661* (2006.01)
*C07F 9/12* (2006.01)
(52) U.S. Cl. ............ 514/114; 514/129; 514/143; 562/23
(58) Field of Classification Search .................. None
See application file for complete search history.

(56) References Cited

U.S. PATENT DOCUMENTS

| | | | |
|---|---|---|---|
| 4,535,186 | A | 8/1985 | Husbands et al. |
| 5,506,270 | A | 4/1996 | Upton et al. |
| 5,530,013 | A | 6/1996 | Husbands et al. |
| 5,554,383 | A | 9/1996 | Dodman |
| 5,788,986 | A | 8/1998 | Dodman |
| 5,916,923 | A | 6/1999 | Rudolph et al. |
| 6,274,171 | B1 | 8/2001 | Sherman et al. |
| 6,310,101 | B1 | 10/2001 | Rudolph et al. |
| 6,348,494 | B1 | 2/2002 | Yardley et al. |
| 6,403,120 | B1 | 6/2002 | Sherman et al. |
| 6,419,958 | B2 | 7/2002 | Sherman et al. |
| 6,444,708 | B2 | 9/2002 | Rudolph et al. |
| 6,673,838 | B2 | 1/2004 | Hadfield et al. |
| 6,696,496 | B2 | 2/2004 | Oosterbaan et al. |
| 2007/0098797 | A1 | 5/2007 | Zhou et al. |

FOREIGN PATENT DOCUMENTS
WO    00/32555 A1    6/2000
WO    02/064543 A2   8/2002

OTHER PUBLICATIONS

Muth et al. Drug Development Research 1991, 23 (2), 191-199.*
Ettmayer et al. Journal of Medicinal Chemistry 2004, 47 (10), 2393-2404.*
Stella V. J, in Prodrugs: Challenges and Rewards, Springer New York, 2007, Chapter 1, pp. 16-17.*
Hobbs, J. B., in Organophosphorous Chemistry, vol. 13, The Royal Society of Chemistry, 1982, Chapter 9, Nucleotides and Nucleic Acids, pp. 175-176.*
Sadock, in Kaplan & Sadock's Pocket Handbook of Psychiatric Drug Treatment, 4th Edition, Lippincott Williams & Wilkins Philadelphia 2006, Chapter 27, p. 187-190.*
Alzheimer's Association Fact Sheet Mar. 2012.*

* cited by examiner

Primary Examiner — Sreeni Padmanabhan
Assistant Examiner — Irina Neagu
(74) Attorney, Agent, or Firm — Lucas & Mercanti, LLP

(57) ABSTRACT

The present invention relates to a novel {4-[2-(dimethylamino)-1-(1-hydroxycyclohexyl)ethyl]phenoxy}phosphate or a pharmaceutically acceptable salt thereof, a production method therefor and a pharmaceutical composition for preventing and treating central nervous system disorders which contains the same as an active component. The novel {4-[2-(dimethylamino)-1-(1-hydroxycyclohexyl)ethyl] phenoxy}phosphate or a pharmaceutically acceptable salt thereof according to the present invention can beneficially be used to prevent and treat central nervous system disorders since it exhibits an equivalent biological and pharmacological activity to venlafaxine and salts thereof which are known in the field, it has very little toxicity, and, in particular, it is outstandingly soluble in water as compared with prior-art venlafaxine derivatives.

9 Claims, No Drawings

{4-[2-(DIMETHYLAMINO)-1-(1-HYDROXYCYCLOHEXYL)ETHYL]PHENOXY}PHOSPHATE OR A PHARMACEUTICALLY ACCEPTABLE SALT THEREOF, A PRODUCTION METHOD THEREFOR AND A PHARMACEUTICAL COMPOSITION FOR PREVENTING AND TREATING CENTRAL NERVOUS SYSTEM DISORDERS CONTAINING THE SAME AS AN ACTIVE COMPONENT

CROSS-REFERENCE TO RELATED APPLICATIONS

This application is a 371 of PCT/KR2009/002426 filed May 8, 2009, which claims the benefit of Korean Application No. 10-2008-0043034 filed May 8, 2008, the contents of each of which are incorporated herein by reference.

TECHNICAL FIELD

The present invention relates to a novel {4-[2-(dimethylamino)-1-(1-hydroxycyclohexyl)ethyl]phenoxy}phosphate or a pharmaceutically acceptable salt thereof, a preparation method thereof, and a pharmaceutical composition for preventing and treating central nervous system disorders comprising the same as an active ingredient.

BACKGROUND ART

Neurotransmitters are in charge of transmission of stimulation by nerves and functions of major organs. Neurotransmitters are classified as cholinergic nervous system, releasing acetylcholine by the stimulation in the central nervous system and peripheral nervous system, adrenergic nervous system, releasing noradrenalin, and other neurotransmitters significant in the central nervous system such as dopamine, serotonine, inhibitory GABA (γ-amino butyric acid). Among those, serotonine nervous system is closely related to mental illnesses such as concerns, anxiety or depression. Schizophrenic or patients with dimentia have noticeably decreased dispersion of receptors of the neurotransmitters. Serotonine in brain is known as an important neuro transmitting network controlling behaviors caused by concerns, anxiety, and physical functions to regulate various physiological functions and mental status.

In the central nervous system, serotonine (5-HT) is related with factors of many diseases, especially mental illnesses such as depression, anxiety, schizophrenia, eating disorders, obsessive compulsive disorder, migraine, panic disorder. In recent, due to the development of pharmacology, molecular biology, genetics relating serotonine nervous system, enhanced medicinal therapies to cure a certain disease of central nervous system are now available. The general treatment for such diseases for now is to regulate physiological activities of serotonine materials.

A major metabolite of venlafaxine, O-desmethylvenlafaxine (hereinafter, referred to as "ODV"), has been shown to inhibit serotonine and norepinephrine reuptake (Klamerus, K. J. et al, "Introduction of the Composite Parameter to the Pharmacokinetics of Venlafaxine and its Active O-Desmethyl Metabolite", J. Clin. Pharmacol. 32:716-724 1992). Therefore, ODV is used to treat diseases of central nervous system, especially, depression or generalized anxiety disorder (see U.S. Pat. No. 5,916,923; U.S. Pat. No. 6,444,708; U.S. Pat. No. 6,274,171; U.S. Pat. No. 6,403,120; U.S. Pat. No. 6,419,958; U.S. Pat. No. 6,310,101). Venlafaxine hydrochloride tablets are available in the market under the product name, EFFEXOR®.

ODV, chemically named 1-(2-(dimethylamino)-1-(4-phenol)ethyl)cyclohexanol, is exemplified as fumarate salt in U.S. Pat. No. 4,535,186. However, the fumarate salt of ODV has unsuitable physicochemical and permeability characteristics. ODV is also exemplified as a free base in International Patent Publication No. WO 00/32555.

The prior art of ODV will be explained below.

Succinate form of ODV is disclosed in U.S. Pat. No. 6,673,838. Succinate monohydrate form of ODV is widely known as sustained-release tablets to relieve side effects such as nausea, vomit, diarrhea or stomachache.

In International Patent Publication No. WO 02/064543 A2, dosage form representing the use of hydroxypropyl methyl cellulose (HPMC) as hydrogel matrix is disclosed.

In U.S. Pat. No. 4,535,186, (R/S)-1-(2-(dimethylamino)-1-(4-methoxyphenyl)ethyl)cyclohexanol and its metabolite, 1-(2-(dimethylamino)-1-(4-methoxyphenyl)ethyl)cyclohexanol and 1-(1-(4-methoxyphenyl)-2-(methylamino)ethyl)cyclohexanol are disclosed.

In U.S. Pat. No. 5,530,013, the use of venlafaxine to induce improved cognitive power is disclosed.

In U.S. Pat. No. 5,506,270, the use of venlafaxine to treat hypothalamic amenorrhea of women with no depression is disclosed.

In U.S. Pat. No. 5,788,986 and U.S. Pat. No. 5,554,383, the use of serotonine reuptake inhibitor to change the habit of dogs is disclosed.

In U.S. Pat. No. 6,348,494, ether of ODV, especially, O-α-acyloxyalkyl ether of 4-(2-(dimethylamino)-1-(1-hydroxycyclohexyl)ethyl)phenol, its preparation method, and pharmaceutical composition and use thereof are disclosed.

However, the above-mentioned materials have problems of low solubility in water.

Accordingly, the present inventors tried to develop ODV derivatives which have high water solubility, but does not affect ODV activity level, and completed the present invention by confirming that the compound of {4-[2-(dimethylamino)-1-(1-hydroxycyclohexyl)ethyl]phenoxy}phosphate has high water solubility and similar activity compared to other salt of ODV.

DISCLOSURE OF INVENTION

Technical Problem

It is an object of the present invention to provide a novel {4-[2-(dimethylamino)-1-(1-hydroxycyclohexyl)ethyl]phenoxy}phosphate.

It is another object of the present invention to provide a preparation method of the {4-[2-(dimethylamino)-1-(1-hydroxycyclohexyl)ethyl]phenoxy}phosphate.

It is yet another object of the present invention to provide a composition comprising the {4-[2-(dimethylamino)-1-(1-hydroxycyclohexyl)ethyl]phenoxy}phosphate as an active ingredient for the prevention and treatment of central nervous system disorders.

Technical Solution

To achieve the above-mentioned objects of the present invention, one embodiment of the present invention provides a novel {4-[2-(dimethylamino)-1-(1-hydroxycyclohexyl)ethyl]phenoxy}phosphate or a pharmaceutically-acceptable salt thereof.

In another embodiment, a preparation method of {4-[2-(dimethylamino)-1-(1-hydroxycyclohexyl)ethyl]phenoxy}phosphate is provided, comprising reacting the compound of Chemical Formula 2 with phosphorylating agent in the presence of solvent and amine to form the {4-[2-(dimethylamino)-1-(1-hydroxycyclohexyl)ethyl]phenoxy}phosphate.

In yet another embodiment, a pharmaceutical composition for the prevention and treatment of central nervous system disorders comprising {4-[2-(dimethylamino)-1-(1-hydroxy-cyclohexyl)ethyl]phenoxy}phosphate or pharmaceutically acceptable salts thereof as an active ingredient, is provided.

Advantageous Effects

The novel {4-[2-(dimethylamino)-1-(1-hydroxycyclo-hexyl)ethyl]phenoxy}phosphate or a pharmaceutically acceptable salt thereof according to the present invention can beneficially be used to prevent and treat central nervous system disorders since it exhibits an equivalent biological and pharmacological activity to venlafaxine and salts thereof which are known in the field, it has very little toxicity, and, in particular, it is outstandingly soluble in water as compared with prior-art venlafaxine derivatives. Furthermore, the {4-[2-(dimethylamino)-1-(1-hydroxycyclohexyl)ethyl] phenoxy}phosphate or pharmaceutically-acceptable salt thereof according to an embodiment of the present invention can be efficaciously used to enhance cognitive power and prescribe for prevention or treatment of smoking.

BEST MODE

The present invention provides a novel {4-[2-(dimethylamino)-1-(1-hydroxycyclohexyl)ethyl]phenoxy}phosphate represented by the following Chemical Formula 1, a pharmaceutically acceptable salt thereof, or isomers thereof:

[Chemical Formula 1]

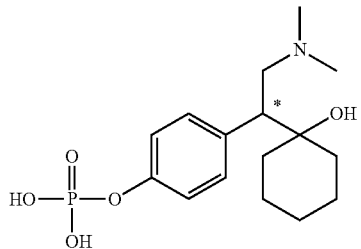

(wherein, "*" represents stereocentre, and coordinations thereof are R, S or racemate.)

The compound of Chemical Formula 1 is active pharmaceutical phosphate of the venlafaxine metabolite, i.e., 4-(2-(dimethylamino)-1-(1-hydroxycyclohexyl)ethyl)phenoxy, which is colorless solid with molecular formula $C_{16}H_{26}NO_5P$ and molecular weight 343.36.

In one embodiment, in addition to the compound of Chemical Formula 1 or pharmaceutically acceptable salt thereof, all the isomer, solvate, or hydrate which may be prepared from the compound of Chemical Formula 1 or pharmaceutically acceptable salt thereof, may be provided.

The compound of the present invention, represented by the Chemical Formula 1, may be used in the form of pharmaceutically acceptable salts. Useful salts are acid addition salts having pharmaceutically acceptable free acids. The acid addition salts may be obtained from inorganic acid such as hydrochloric acid, nitric acid, phosphoric acid, sulfuric acid, hydrobromic acid, hydriodic acid, nitrous acid or phosphorous acid, and nontoxic organic acids such as aliphatic mono and dicarboxylate, phenyl-substituted alkanoate, hydroxyalkanoate, alkanedioate, aromatic acid, aliphatic and aromatic sulphonic acid. These pharmaceutically nontoxic salts comprise sulfate, ferric sulfate, bisulfate, sulfite, bisulfite, nitrate, phosphate, monohydrogen phosphate, dihydrogen phosphate, metaphosphate, ferric phosphate chloride, bromide, iodide, fluoride, acetate, propionate, decanoate, caprylate, acrylate, formate, isobutyrate, caprate, heptanoate, phenylpropiolate, oxalate, malonate, succinate, suberate, sebacate, fumarate, maleate, butine-1,4-dioate, hexane-1,6-dioate, benzoate, chlorobenzoate, methylbenzoate, dinitro benzoate, hydroxybenzoate, methoxybenzoate, phthalate, terephthalate, benzene sulfonate, toluene sulfonate, chlorobenzene sulfonate, xylenesulfonate, phenyl acetate, phenylpropionate, phenylbutyrate, citrate, lactate, D-hydroxybutyrate, glicolate, maleate, tartrate, methanesulfonate, propanesulfonate, naphthalene-1-sulfonate, naphthalene-2-sulfonate or mandelate.

Acid addition salts according to the present invention may be prepared using a conventional method. For example, they may be prepared by dissolving the compound of Chemical Formula 1 in a water-miscible organic solvent, such as acetone, methanol, ethanol or acetonitrile and adding an excess of organic acids or an excess of aqueous inorganic acid solutions so as to precipitate or crystallize salts. These acid addition salts may be obtained by distilling the solvent or excess of acids from the solution or by suctioning and filtering the precipitates.

Also, pharmaceutically acceptable metallic salts may be prepared by using base. Alkali metals or alkali earth metals salt, for example, may be obtained by melting the compound in an excessive amount of alkali metal hydroxide or alkali earth metals hydroxide, filtering non-soluble composition salt, and evaporating and drying residual solvent. The metallic salt may be sodium salt, potassium salt or calcium salt. Further, silver salts corresponding to the metallic salts may be obtained by reacting alkali metals or alkali earth metals with suitable silver salts (such as silver nitrate).

Also, an embodiment of the present invention provides a novel {4-[2-(dimethylamino)-1-(1-hydroxycyclohexyl)ethyl]phenoxy}phosphate (hereinafter, referred to as 'ODV phosphate').

The novel ODV phosphate according to the present invention, as illustrated by the following Reaction Scheme 1, may be synthesized by reacting Chemical Formula 2 with phosphorylating agent in the presence of solvent and amine.

[Reaction Scheme 1]

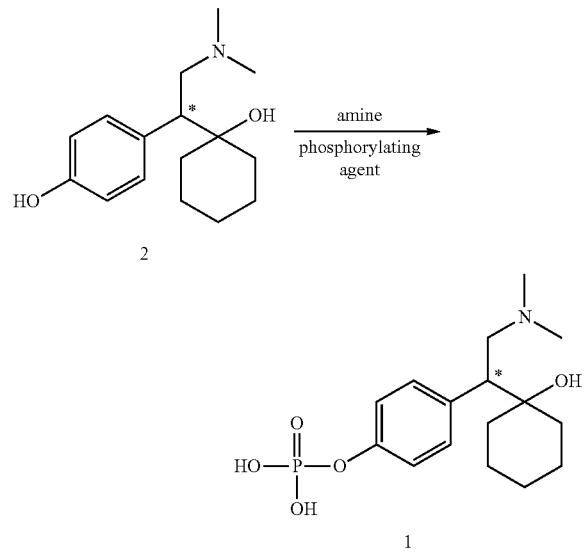

(wherein, the "*" is same as defined in Chemical Formula 1.)

The starting material, i.e., 1-(2-(dimethylamino)-1-(4-hydroxycyclohexyl)ethyl)cyclohexanol racemic compound of Chemical Formula 2 may be prepared by the method disclosed in Example 26 of U.S. Pat. No. 4,535,186. Here, enantiomers may be divided by standard resolution technique widely known in the prior art, and may be obtained from O-demethylation of enantiomers separated from venlafaxine using boron tribromide or ethanedithiol anion.

In the preparation method according to the present invention, the solvent may be inert solvent such as acetonitrile, tetrahydrofuran or dimethylformamide, but not limited thereto.

In the preparation method according to the present invention, the amine may be triethylamine (TEA), diethylamine (DEA), diisopropylethylamine, cyclohexylamine or diisopropylamine, but not limited thereto.

In the preparation method according to the present invention, the phosphorylating agent may be phosphorus oxychloride, halophosphate diester, but not limited thereto.

The phosphorylating agent may be any reagent which can phosphorylate phenols.

In the preparation method according to the present invention, the temperatures may range between 0~5° C. Otherwise, the efficiency of reaction may deteriorate and the side effects may be happened.

An embodiment of the present invention provides a composition for the prevention and treatment of central nervous system disorders comprising the compound of Chemical Formula 1 or a pharmaceutically acceptable salt thereof as an active ingredient.

An embodiment of the present invention provides a method for preventing or treating central nervous system disorders in a subject comprising administering an effective amount of the compound of Chemical Formula 1 or a pharmaceutically acceptable salt thereof to the subject.

The compound of Chemical Formula 1 or pharmaceutically acceptable salt thereof according to the present invention has the activities equivalent to the biological and pharmaceutical activities generally-used venlafaxine and salt thereof, as well as has little toxicity, and superior water solubility to the conventional venlafaxine derivatives, and therefore, may be used for treatment or relief of central nervous system disorders such as depression (including major depressive disorder, bipolar disorder and mild depression), fibromyalgia, anxiety, panic disorder, agoraphobia, post traumatic stress disorder, premenstrual dysphoric disorder (premenstrual syndrome), attention deficit disorder, obsessive compulsive personality disorder (including trichotillomania), social anxiety disorder, generalized anxiety disorder, autism, schizophrenia, obesity, anorexia nervosa, bulimia nervosa, tourette syndrome (Gilles de la Tourette Syndrome), vasomotor flushing, cocaine and alcohol addiction, sexual dysfunction (including premature ejaculation), borderline personality disorder, chronic fatigue syndrome, urinary incontinence, pain (including chronic back pain, phantom limb pain, central pain, neuropathy such as diabetic neuropathy, postherpetic neuralgia), or Raynaud's syndrome. Furthermore, the compound of Chemical Formula 1 or pharmaceutically acceptable salt thereof according to the present invention may be used for enhancing cognitive power and prescribe for prevention or treatment of smoking and drinking.

The composition comprising the compound of Chemical Formula 1 or pharmaceutically acceptable salt thereof as an active ingredient may be used as a generally-used medicinal dosage form.

The compound of Chemical Formula 1 according to the present invention may be formulated into various dosage forms, such as oral or parenteral administration. When formulated, the composition may be prepared including one or more pharmaceutically available carriers as well as effective ingredients.

The pharmaceutically available carriers may be saline, sterile water, ringer's solution, buffered saline, dextrose solution, maltodextrin solution, glycerol, ethanol, and if necessary, other addictives such as antioxidant, suffer solution, bacteriostatic agent may be added.

Solid formations for oral administration may include tablets, pills, granules or capsules, and the solid formations may be prepared by mixing one or more of diluting agents such as calcium carbonate, sucrose, lactose or gelatin. In addition to the diluting agents, lubricant such as magnesium stearate talc is also used.

Liquid formations for oral administration, comprising emulsion, content solvent, syrup, etc., may include simple diluents such as water or liquid paraffin, as well as a various diluting agent such as humectant, sweeting agents, air freshener, or preservatives. Formulations for parenteral administration may be sterilized aqueous solution, nonaqueous solvent, emulsion, freeze drying agent or suppository. Nonaqueous solution and emulsion may be propylene glycol, polyethylene glycol, vegetable oil such as olive oil, ester available for injection such as ethyl oleate. Formations for suppository may include witepsol, macrogol, tween 61, cacao oil, laurin oil, glycerol or gelatin.

Pharmaceutical compositions according to the present invention may be administered parenterally by subcutaneous injection, intravenous injection or vastus lateralic injection. Formations for parenteral administration may include mixing the composition with stabilizing agent or buffer agent in water to prepare solution or suspension, and forming ample or vial form.

It is desirable that the weight of composition may be 0.1~50 weight % of the all weight, but not limited thereto. Depending on the condition of patients or kinds of disease and progressing status, the weight may vary.

The desirable injecting amount of the composition according to an embodiment of the present invention may vary depending on the condition and weight of patients, kinds of disease, forms of drugs, injecting route and period, and those of ordinary skill in the art may adjust the amount appropriately about 0.01 mg/kg to about 10 g/kg in a day, preferably about 1 mg/kg to about 1 g/kg in a day. The injection may be done once or more times in a day.

MODE FOR THE INVENTION

A better understanding of the present invention may be obtained through the following examples which are set forth to illustrate, but are not to be construed as the limit of the present invention.

Example

Synthesis of {4-[2-(dimethylamino)-1-(1-hydroxycyclohexyl)ethyl]phenoxy}phosphate (ODV phosphate)

4-(2-(dimethylamino)-1-(1-hydroxycyclohexyl)ethyl) phenoxy (26.33 g, 0.1 mol) was put into tetrahydrofuran (1.2 L), dissolved at 45° C. and frozen at 0~5° C. Triethylamine (61.52 mL, 0.44 mol) was put, stirred for 20 minutes, phosphorous oxychloride (10.06 mL, 0.11 mol) was added dropwise, and stirred for one hour at 0~5° C. After the chemical reaction is completed, tetrahydrofuran (200 mL) and deionized water (200 mL) were added. The compound was stirred for two hours at a room temperature and concentrated. The compound was crystallized as methanol and chloroform to form the pure colorless solid composition (24 g, 70%).

$^1$H NMR (D$_2$O) δ 1.15-1.54 (m, 9H), 1.72 (d, 1H), 2.81 (s, 3H), 2.87 (s, 3H), 3.15 (dd, 1H), 3.62 (dd, 1H), 3.79 (t, 1H), 7.24 (d, 2H), 7.40 (d, 2H);

$^{13}$C NMR (D$_2$O) δ 21.40, 21.69, 25.24, 34.57, 35.30, 41.73, 45.59, 50.78, 58.73, 73.58, 121.23, 121.27, 131.64, 152.33, 152.40.

Experimental Example 1

Measurement of Solubility

Experiment was conducted to measure water solubility of ODV phosphate compound of the present invention.
(1) Preparation of Internal Standard Substance
100 mg of venlafaxine, as internal standard (ISTD), was mixed in water to form 500 mL of the mixture to improve accuracy.
(2) Setting of Calibration Curve
40, 50 and 60 mg of ODV phosphate composition prepared by the embodiment was mixed in 100 mL of water to form 0.4, 0.5 and 0.6 mg/mL concentration of ODV phosphate solution respectively. The above ODV phosphate solution and internal standard substance were analyzed with HPLC to measure ODV phosphate according to the concentration of ODV phosphate and peak area ratio of internal standard substance, and a calibration curve was set. The HPLC analysis was done many times to measure the average value of the calibration curve.

The conditions of HPLC analysis are listed in Table 1 and Table 2.

TABLE 1

| Column | ODS, 5 μm, 4.6 × 250 mm |
|---|---|
| Injection volume | 20 μL |
| Mobile phase | (A)Phosphate butter solution/(B)Acetonitrile |
| Flow rate | 1.5 mL/min |
| Detection | 226 nm |

*Preparation of phosphate butter solution: 8.89 g of Na$_2$HPO$_4$•2H$_2$O and 2.5 g of sodium 1-octanesulfonate was dissolved in 1000 mL of water, 10% of H$_3$PO$_4$ was added, pH was adjusted to 3.0, and filtered to form phosphate butter solution.

TABLE 2

| Gradient Condition | | | |
|---|---|---|---|
| Stage | Time | Mobile phase A | Mobile phase B |
| 0 | 00 | 70 | 30 |
| 1 | 05 | 70 | 30 |
| 2 | 30 | 30 | 70 |
| 3 | 35 | 30 | 70 |
| 4 | 40 | 70 | 30 |
| 5 | 45 | 70 | 30 |

(3) Measurement of Solubility

An excessive amount of ODV phosphate compound (approximately 400 mg) prepared by the embodiment was dissolved in 2 mL of water and filtered to form a saturated solution. 1 mL of the above saturated solution was diluted with water to prepare 20 mL of solution. The diluting process was repeated many times to form saturated solution with 800 times of dilution rate. This solution and internal standard substance were analyzed with HPLC to measure ODV phosphate and peak area ratio of internal standard. The measured value was substituted in calibration curve to calculate the concentration, and multiply the dilution rate to measure solubility.

In a comparative example, ODV succinate compound, which is usually used, was used. Except the fact that the conventional ODV succinate compound has the concentration of 0.1, 0.15, and 0.2 mg/mL when the calibration curve is set, the rest of the process is the same as explained above. The result is listed in Table 3.

TABLE 3

| Compound | Solubility (mg/mL) |
|---|---|
| ODV phosphate | 313.4 |
| ODV succinate | 84.2 |

As shown in table 3, ODV phosphate compound according to an embodiment of the present invention has water solubility of 313.4 mg/mL, which is 4 times higher than the solubility (84.2 mg/mL) of ODV compound usually used.

Experimental Example 2

Acute Toxicity Experiment

Experiment was conducted to measure acute toxicity of ODV phosphate compound according to an embodiment of the present invention.

7-week-old ICR mice, weighing 25~35 g each, were used in the experiment (SPF, production firm: coretech). Eight mice, 4 females and 4 males respectively, were intraperitoneally injected with ODV phosphate or 150, 250, 350 and 450 mg/kg of ODV succinate hydrate mixed with 100% distilled water, and as a control group, mice were injected with only distilled water for 7 days to measure the number of dead mice and acute toxicity level of chemicals. The results are listed in Table 4.

TABLE 4

| | | The number of death mice according to experimental days | | | | | | |
|---|---|---|---|---|---|---|---|---|
| Group | Dose (mg/kg) | Day 1 | Day 2 | Day 3 | Day 4 | Day 5 | Day 6 | Day 7 |
| Control | — | — | — | — | — | — | — | — |
| ODV Phosphate | 150 | — | — | — | — | — | — | — |
| | 250 | — | — | — | — | — | — | — |
| | 350 | — | — | — | — | — | — | — |
| | 450 | — | — | — | — | — | — | — |
| ODV succinate | 150 | — | — | — | — | — | — | — |
| | 250 | — | — | — | — | — | — | — |
| | 350 | 2 | — | — | — | — | — | — |
| | 450 | 8 | | | | | | |

As shown in table 4, with the use of 350 mg/kg of ODV succinate hydrate, 2 mice were dead on day 1, and with the use of 450 mg/kg of ODV, all the 8 mice were dead on day 1. However, when 450 mg/kg of ODV phosphate compound according to an embodiment of the present invention was injected, no mice were dead for 7 days. Therefore, ODV phosphate compound of the present invention is proved to be stable and have little toxicity.

Experimental Example 3

Pharmacokinetics Experiment 9-week-old female mice, SD rats, weighing 320±20 g each, were used in the experiment (SPF, production firm: coretech). ODV phosphate compound prepared by the embodiment was dissolved in solvent (100% distilled water) and 120 mg/kg of the same was orally administered to 3 mice. After 0.08, 0.25, 0.5, 1, 2, 3, 4, 6 hours of administration, blood was taken from mice, and separated by centrifuge. The concentration of the separated blood was measured with LC/MS/MS. As a comparative example, ODV succinate hydrate was measured in the same manner explained above. The results are listed in Table 5.

$C_{max}$ is the highest concentration level of blood in body, $T_{max}$ is the time to reach the highest concentration level of blood, $AUC_{0-t}$ is square between blood concentration to time and time, $AUC_{0-inf}$ is square between blood concentration and time, and $t_{1/2}$ is half-life of compound in body, and $MRT_{inf}$ is remaining period of compound in body.

TABLE 5

|  |  | ODV succinate | ODV phosphate |
|---|---|---|---|
| Amount | (mg/kg) | 120.0 | 120.0 |
| $T_{max}$ | (hr) | 0.5 | 0.5 |
| $C_{max}$ | (ng/ml) | 2786.7 | 4696.7 |
| $AUC_{0-t}$ | (hr · ng/ml) | 7017.4 | 9833.2 |
| $AUC_{0-inf}$ | (hr · ng/ml) | 9268.8 | 12163.5 |
| $t_{1/2}$ | (hr) | 5.0 | 4.7 |
| $MRT_{inf}$ | (hr) | 5.7 | 4.6 |

As shown in table 5, $C_{max}$ and $AUC_{0-inf}$ of ODV phosphate compound are noticeably higher than those of ODV succinate hydrate, which increase bioavailability and have same effect with the use of an amount lesser than ODV succinate hydrate.

Therefore, the ODV phosphate compound according to an embodiment of the present invention has superior water solubility, stability with little toxicity and has the same pharmaceutical effect as the ODV compound generally used. Therefore, the ODV phosphate can be used as a replacement of ODV compound generally used for treatment of diseases.

Preparation Example 1

Preparation of Pharmaceutical Formulations

<1-1> Preparation of Powders 2 g of compound of Chemical Formula 1
1 g of lactose
Powders were prepared by mixing the above compounds, and filling the mixture in an air-tight container.

<1-2> Preparation of Tablets 100 mg of compound of Chemical Formula 1
100 mg of corn starch
100 mg of lactose
2 mg of stearic acid magnesium
Tablets were prepared by mixing the above compounds, and pressing the mixture according to the general preparation method.

<1-3> Preparation of Capsules 100 mg of compound of Chemical Formula 1
100 mg of corn starch
100 mg of lactose
2 mg of stearic acid magnesium
Capsules were prepared by mixing the above compounds, and filling the mixture in gelatine capsules according to the general preparation method.

<1-4> Preparation of Injection Liquid 10 mg/ml of compound of Chemical Formula 1
dilute hydrochloric acid with BP pH 3.5
maximum 1 ml of sodium chloride BP for injection Injection liquid was prepared by dissolving an appropriate amount of sodium chloride BP for injection in the compound of Chemical Formula 1, regulating the pH value of the compound to pH 3.5 with dilute hydrochloric acid, adjusting volume using sodium chloride BP for injection, and mixing the liquid sufficiently. The solution was filled in 5 ml of type I plain glass ampoule, the glass was sealed at the top, and sterilized at 120° C. for 15 minutes or longer.

The invention claimed is:

1. A compound of {4-[2-(dimethylamino)-1-(1-hydroxycyclohexyl)ethyl]phenoxy}phosphate having the following Chemical Formula 1, a pharmaceutically acceptable salt thereof, stereoisomers, or a mixture thereof:

[Chemical Formula 1]

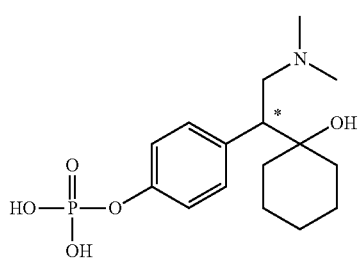

wherein, the configuration at the stereocenter (*) may be R, S, or RS (a racemate).

2. A method of preparing the compound of claim 1 comprising:
   reacting a compound of Chemical Formula 2 with a phosphorylating agent in the presence of solvent and amine to form {4-[2-(dimethylamino)-1-(1-hydroxycyclohexyl)ethyl]phenoxy}phosphate as the following Reaction Scheme 1:

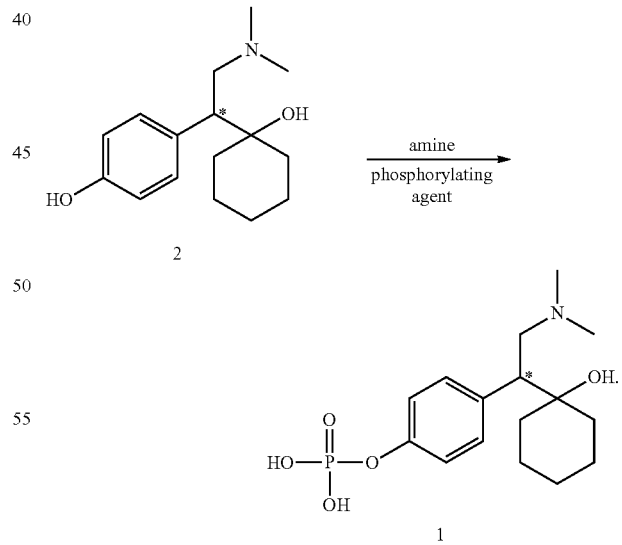

3. The method according to claim 2, wherein the solvent is acetonitrile, tetrahydrofuran, or dimethyl formamide.

4. The method according to claim 2, wherein the amine is selected from triethylamine (TEA), diethylamine (DEA), diisopropylethylamine, cyclohexylamine and diisopropylamine.

5. The method according to claim 2, wherein the phosphorylating agent is phosphorus oxychloride or halophosphate diester.

6. The method according to claim 2, wherein the reacting is conducted at a temperature of 0~5° C.

7. A pharmaceutical composition for treating depression, social anxiety disorder and generalized anxiety disorder comprising the compound of claim 1 as an active ingredient.

8. A method for treating central nervous system disorders in a subject comprising administering an effective amount of the compound of claim 1 to the subject, wherein the central nervous system disorder is selected from the group consisting of depression, social anxiety disorder and generalized anxiety disorder.

9. The method according to claim 8, wherein the depression comprises major depressive disorder, bipolar disorder, and dysthymic disorder.

* * * * *